(12) United States Patent
Asami et al.

(10) Patent No.: US 9,067,053 B2
(45) Date of Patent: Jun. 30, 2015

(54) ULTRASONIC TREATMENT DEVICE (75) Inventors: Rei Asami, Kokubunji (JP); Kenichi Kawabata, Kodaira (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 13/395,198

(22) PCT Filed: Dec. 1, 2010

(86) PCT No.: PCT/JP2010/071428
§ 371 (c)(1),
(2), (4) Date: Mar. 9, 2012

(87) PCT Pub. No.: WO2011/068108
PCT Pub. Date: Jun. 9, 2011

(65) Prior Publication Data
US 2012/0172720 A1 Jul. 5, 2012

(30) Foreign Application Priority Data
Dec. 4, 2009 (JP) .................................. 2009-276731

(51) Int. Cl.
*A61B 6/00* (2006.01)
*A61N 7/02* (2006.01)
*A61B 17/00* (2006.01)
*A61B 17/22* (2006.01)
*A61N 7/00* (2006.01)

(52) U.S. Cl.
CPC ......... *A61N 7/02* (2013.01); *A61B 2017/00176* (2013.01); *A61B 2017/22089* (2013.01); *A61N 2007/0039* (2013.01)

(58) Field of Classification Search
USPC .................. 600/431–432, 437, 407, 427–428
See application file for complete search history.

(56) References Cited

U.S. PATENT DOCUMENTS

| | | | |
|---|---|---|---|
| 2002/0129656 A1* | 9/2002 | Tsuzuki | 73/620 |
| 2003/0018256 A1 | 1/2003 | Sasaki et al. | |
| 2003/0206864 A1 | 11/2003 | Mangin | |
| 2004/0253183 A1* | 12/2004 | Uber et al. | 424/9.52 |
| 2005/0038340 A1* | 2/2005 | Vaezy et al. | 600/439 |
| 2006/0158956 A1* | 7/2006 | Laugharn et al. | 366/127 |
| 2007/0016042 A1 | 1/2007 | Kawabata et al. | |

(Continued)

FOREIGN PATENT DOCUMENTS

| | | |
|---|---|---|
| CN | 1864636 A | 11/2006 |
| CN | 1891167 A | 1/2007 |

(Continued)

OTHER PUBLICATIONS

M. Zhang "Initial Investigation of Acoustic Droplet Vaporization for Occlusion in Canine Kidney" Ultrasound in Med. & Biol, vol. 36, No. 10, pp. 1691-1703 (2010).

(Continued)

*Primary Examiner* — Tse Chen
*Assistant Examiner* — Joel F Brutus
(74) *Attorney, Agent, or Firm* — Miles & Stockbridge P.C.

(57) ABSTRACT

There is provided an ultrasonic treatment device that is minimally-invasive and that achieves embolization treatment having a high blood flow blocking effect. To this end, the ultrasonic treatment device is provided with a function to transmit to a target area of a subject both a bubble generation pulse that vaporizes a contrast agent, and a bubble generation pulse that causes the diameter of the formed bubble to increase.

8 Claims, 5 Drawing Sheets

(56) References Cited

U.S. PATENT DOCUMENTS

| | | |
|---|---|---|
| 2007/0038099 A1 | 2/2007 | Sugita et al. |
| 2007/0161897 A1 | 7/2007 | Sasaki et al. |
| 2007/0161902 A1 | 7/2007 | Dan |
| 2008/0200815 A1* | 8/2008 | Van Der Steen et al. ..... 600/467 |
| 2008/0208054 A1* | 8/2008 | Azuma et al. ................. 600/443 |
| 2010/0158816 A1 | 6/2010 | Kawabata et al. |
| 2010/0228122 A1* | 9/2010 | Keenan et al. ................ 600/432 |

FOREIGN PATENT DOCUMENTS

| | | |
|---|---|---|
| CN | 101164533 A | 4/2008 |
| JP | 2003-33365 A | 2/2003 |
| JP | 2003-525682 A | 9/2003 |
| JP | 2007-000218 A | 1/2007 |
| JP | 2007-520307 | 7/2007 |
| JP | 2008-24604 A | 2/2008 |
| WO | WO 2004/100811 A1 | 11/2004 |

OTHER PUBLICATIONS

Office Action issued Jan. 20, 2014, in Chinese Patent Application No. 201080040199.0.

* cited by examiner

Comment: Arrows indicate foci of ultrasonic pulses

Fig. 6 ic wave treatment. For example, the present invention relates to a device used in embolization therapies that achieve treatment effect by occluding blood vessels in the neighborhood of an area of pathology, such as a tumor.

ULTRASONIC TREATMENT DEVICE

TECHNICAL FIELD

The present invention relates to a device for ultrasonic wave treatment. For example, the present invention relates to a device used in embolization therapies that achieve treatment effect by occluding blood vessels in the neighborhood of an area of pathology, such as a tumor.

BACKGROUND ART

With steadily growing case rates of cancer, which is classified as one of three major diseases in Japan, there are strong desires for useful methods for early diagnosis and treatment thereof. Research and development has actively been advancing, in particular, for medical image diagnostic apparatuses that afford quite an early discovery and identification of cancers. Advances in technology are marked in multiple modalities, including positron emission tomography (PET), Computed Tomography (CT), and magnetic resonance imaging (MRI), and ultrasonic wave. However, even with an early discovery, surgical operations and radiation treatments involve high risks and adverse reactions. Therefore, there are some cases where it is difficult to determine to embark on the treatment. For this reason, research and development is imperative of a method for minimally-invasive therapy, which accommodates to the early discovery.

One such advancing research for minimally-invasive therapies is of an embolization therapy. An embolization therapy is a method for treatment, which yields a treatment effect by necrotizing localized diseases, i.e. an original tumor, a hysteromyoma, and so on, by blocking nutrient vessels. More specifically, there is used a method for occluding a blood vessel, in which a catheter is inserted to a nutrient vessel of a tumor to inject an embolic agent thereinto under X-ray monitoring.

However, this method of treatment involves possibility that the embolic agent causes occlusion of blood vessels connecting to normal tissues, and there is always the risk that the normal tissues are also necrotized. Moreover, due to the usage of catheter, this treatment requires to be performed under local or general anesthesia of the patient. Moreover, it has been pointed out that this method for treatment is not necessarily minimally invasive since it uses X-ray for monitoring.

Then, in order to achieve less invasivity of the embolization therapy, various methods have been developed from respective viewpoints of monitoring, embolic agents and transfer techniques. First, a method has been reported that uses bubbles, not a solid substance, as an embolic agent (Patent Literature 1). In this method, monitoring can be performed by using ultrasonic wave, instead of X-ray, and therefore reduction of exposure to X-ray is expected. Further, Patent Literature 2 discloses a method in which a liquid medical agent is administered in a biological body in advance, and external stimulus is applied to a target position to cause the medical agent to form into bubbles, thereby blocking the blood flow to and from a tumor. Further, Patent Literature 3 discloses a method in which insertion of embolic agent using a catheter is not used, i.e. a method that blocks blood flow by applying focused ultrasonic wave to a target blood vessel and denaturing the blood vessel. Furthermore, Patent Literature 4 discloses a method in which bubbles are locally formed by using ultrasonic wave energy, and the generated bubbles are used to implement the embolization therapy.

However, all of the above-stated methods for minimally-invasive embolization therapy have problems in certainty of the treatment. For example, in the method using bubbles, it is difficult to achieve the effect of occlusion unless considerable amount of bubbles are stably supplied into the blood vessels to embolize them, because, while the size of a micro bubble used in this method is no greater than 1-5 μm or so, the diameters of capillary vessels in a tumor are 10-40 μm and, moreover, the diameter of major arterial vessels connecting to the tumor is 1 mm or greater. Administration of a material to form into bubbles into a biological body in advance has the same problem in principle. Further, also in the case of applying ultrasonic wave energy to a target blood vessel in order to denature the blood vessel, it is difficult to unfailingly denature a solely one blood vessel, because dislocation is likely to occur between a position where the ultrasonic wave energy converges and a position of a geometric focus of a transducer, due to the effect of attenuation of the ultrasonic wave within the biological body.

CITATION LIST

Patent Literature

Patent Literature 1: JP Patent Publication (Kohyo) No. 2003-525682 A
Patent Literature 2: JP Patent Publication (Kokai) No. 2008-024604 A
Patent Literature 3: JP Patent Publication (Kokai) No. 2007-000218 A
Patent Literature 4: JP Patent Publication (Kohyo) No. 2007-520307 A

SUMMARY OF INVENTION

Technical Problem

As stated above, embolization therapies using conventional techniques have problems of having high invasivity, or minimally-invasivity in compensation for a low blood flow blocking effect. Therefore, it is an object of the present invention to provide a device that can implement an embolization treatment that is minimally-invasive while having a high blood flow blocking effect.

Solution to Problem

The inventors diligently studied to solve the above problem and as an outcome thereof, will provide a device with a function to transmit, to a target area of a subject, a bubble generation pulse that vaporizes a phase-change contrast agent and a bubble stabilization pulse that increases the diameter of the formed bubble.

Advantageous Effect of Invention

According to the present invention, it becomes possible to put to a practical use an embolization treatment that is minimally-invasive while having a high blood flow blocking effect.

DESCRIPTION OF EMBODIMENTS

Basic Principle

The inventors of the present invention found that there are two bubble states, i.e., a transient bubble state in which bubble fade after application of an ultrasonic wave, and a stable bubble state in which bubbles steadily exist after the ultrasonic wave application, through an experiment. In the experiment, variously changed ultrasonic waves are applied to a phase-change contrast agent having a property of being liquid state at administration but vaporized by receiving ultrasonic wave application. The following describes a basic principle for enhancing a blood flow blocking effect utilizing this phenomenon.

Figure 1:
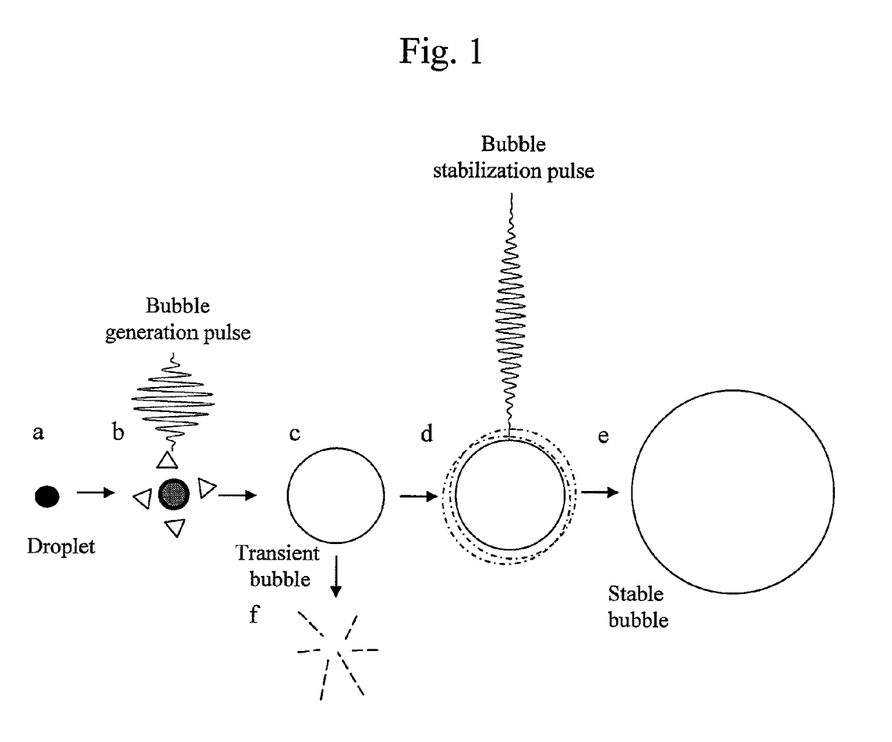
FIG. 1 is a diagram for explaining a response of a phase-change contrast agent to ultrasonic wave application.

FIG. 1 schematically shows the growth of the phase-change contrast agent to the stable bubble state via the transient bubble state. When a bubble generation pulse for vaporizing the contrast agent is applied to the phase-change contrast agent in which a low boiling point compound is microparticulated by a surfactant, the liquid thereinside is brought into a boiling state and vaporized by the effect of the ultrasonic wave (stages a, b, c). The bubbles at this stage are in a transient bubble state, in which the bubbles show such a transient response that they return to a liquid phase when the application of the bubble generation pulse is stopped (stage f).

The inventors attempted to apply a bubble stabilization pulse (stage d) that vibrates the bubbles in the transient bubble state (stage c), successively after the application of the bubble generation pulse. Then, stably existing bubbles with large diameters are formed (stage e). This seems to be ascribed to growth of bubble radii due to incorporation of gas into a bubble from the surrounding medium and integration with transient bubbles existing therearound. Since the ratio of volume to surface of a stable bubble is smaller than that of a transient bubble, it can be persistent more stably. The inventors found that there occur the transient bubble state and the stable bubble state according to the above-described mechanism.

Figure 2:
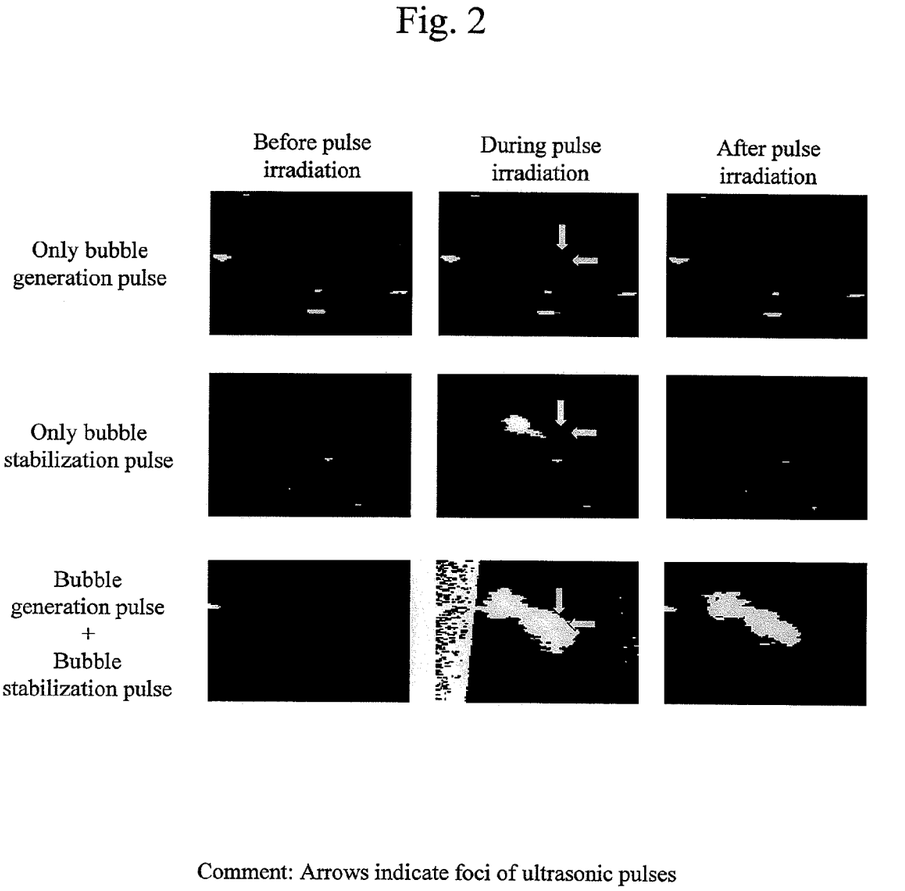
FIG. 2 is a diagram showing resulting responses corresponding to differences in conditions of ultrasonic wave application to the phase-change contrast agent.

FIG. 2 shows a result of the examination in which the difference of bubble formation is examined experimentally. This experiment is as follows: a tissue-mimic phantom, in which the phase-change contrast agent is sealed, is left at rest in a liquid bath filled with degassed water having a temperature of 37 degrees centigrade; a bubble generation pulse is solely applied to the tissue-mimic phantom, or a bubble stabilization pulse is solely applied thereto, or a bubble stabilization pulse is applied successively after the application of the bubble generation pulse; and the state transition of the bubbles is observed on an echographic display. The condition of ultrasonic wave application used in this experiment is as shown in table 1:

TABLE 1

| | bubble generation pulse | bubble stabilization pulse |
| --- | --- | --- |
| central frequency | 3.3 MHz | 1.1 MHz |
| pulse duration | 100 cycles | 10000 cycles |
| ultrasonic wave intensity | 2.4 kW/cm2 | 110 W/cm2 |
| pulse repetition frequency | 12 Hz | 12 Hz |
| time duration of application | 1 sec | 1 sec |

First, a case where the bubble generation pulse is solely applied to the tissue-mimic phantom (the upper row in FIG. 2) will be described. In this case, throughout the pulse irradiation, bubbles are generated at a focus position of the pulse (the position pointed by two arrows in the drawing) and a rapid signal increase occurred. However, at the same time as termination of application, the high brightness disappeared.

Next, a case where the bubble stabilization pulse is solely applied to the tissue-mimic phantom (the middle row in FIG. 2) will be explained. In this case, no particular change occurred at the focus position of the bubble stabilization pulse (the position pointed by two arrows in the drawing).

Finally, a case where a combination of the bubble generation pulse and the bubble stabilization pulse is applied to the tissue-mimic phantom will be explained (the bottom row of FIG. 2). This case is, as explained in FIG. 1, where the bubble stabilization pulse is applied successively after the application of the bubble generation pulse. In this case, during the pulse irradiation, bubbles are formed at the focus position (the position pointed by two arrows in the drawing) of the pulse, and a rapid signal increase occurred. Moreover, this rapid signal increase was persistent after the termination of the pulse irradiation. That is, it is found that bubbles of different persistence can be formed by applying pulses of different kinds to the same ultrasonic wave contrast media.

In light of the above-described experimental results, the inventors got an idea of utilizing the transient response of the phase-change contrast agent for diagnosis and monitoring, while utilizing the stable response for embolization treatment of a blood vessel of a tumor, to came to invent the ultrasonic treatment device used for an embolization treatment on a subject to which a phase-change contrast agent has been administered.

More specifically, the inventors invented an ultrasonic treatment device including a receiving/transmitting sequence controller that performs control of transmission/reception of two kinds of ultrasonic wave pulses that vaporize a phase-change contrast agent respectively in transient and stable manners, a signal monitor that renders a blood flow that is the target of the treatment and, during the treatment in progress, detects the occurrence of a blood flow, and a feedback controller that instructs the receiving/transmitting sequence controller to implement an additional treatment based on the information provided by the signal monitor.

Here, desirably, the frequency of the bubble generation pulse that causes the transient vaporizing is 0.5-10 MHz, and the pulse duration thereof is approximately within 2 ms, and, more desirably, within 1 ms. On the other hand, a bubble stabilization pulse used for stable vaporizing has no special constraint as long as the condition of ultrasonic wave application is such that it can vibrate the bubbles formed by the bubble generation pulse. However, it is desirable that the frequency of the bubble generation pulse is approximately 0.5-10 MHz, and the pulse intensity is no greater than the degree to vaporize the liquid of the contrast agent.

Furthermore, it is desirable that the signal monitor provided for the ultrasonic treatment device extracts an echo signal as the transient response from the phase-change contrast agent to render capillary vessel systems around the tumor that is difficult to render with a normal ultrasonic wave sonography. The signal monitor sets these blood vessels as a treatment target area, and sends position information to a feedback controller. The feedback controller outputs an instruction signal to the receiving/transmitting sequence controller to instruct it to transmit stable vaporizing pulse along with position information, and, in response to the instruction signal, the receiving/transmitting sequence controller transmits a stable vaporizing pulse.

In the portion where the stable bubbles are formed, a blood flow is completely blocked to yield a treatment effect. If the blood flow occurs (i.e. the treatment is in an incomplete condition), inflow of blood and the phase-change contrast agent (liquid) into the treatment target area occurs. In order to detect the blood inflow, it is desirable that the ultrasonic treatment device has a monitoring function to periodically apply the bubble generation pulse to the treatment target area also in the progress of the embolization treatment to extract signals originating from the bubble formation (hereafter referred also to "bubble originating signal".) When the ultrasonic treatment device has this function, the device can instruct the feedback controller to perform additional application of the bubble generation pulse and the bubble stabilization pulse for treatment based on detection of the bubble originating signal to block the blood flow again, thereby enhancing the effect of the embolization treatment.

It is desirable that the signal monitor has a function to detect fading of bubbles in the treatment target area, in addition to the function to detect the above-described bubble originating signal. This function is realized by extracting, as a bubble region, a signal having a predetermined signal intensity or greater of those ultrasonic wave signals detected when the normal image diagnosis pulse is applied to the treatment target area, and detecting contraction (fading) of the bubble region by temporal subtraction of the bubble region. If the ultrasonic treatment device has this function, it becomes possible to instruct the feedback controller to perform additional application of the bubble generation pulse and the bubble stabilization pulse for treatment on detection of the bubble fading, thereby again growing the bubbles to enhance the effect of the embolization treatment.

By employing the above-described basic principle and the mechanism in an ultrasonic treatment device, it becomes possible to attain a more enhanced blood flow blocking effect than with the conventional devices while providing a minimally-invasive embolization therapy involving no direct intrusion of needles or catheters into a diseased part of a subject.

Embodiments

The following describes embodiments of the present invention with reference to drawings. The explanations below of the device configurations and processing operations are provided merely as one example for describing the present invention, and any combination of known techniques to the below-described device configurations and processing operations, or any partial substitution with known techniques of the below-described device configurations and processing operations, are also included in the scope of the present invention.

Figure 3:
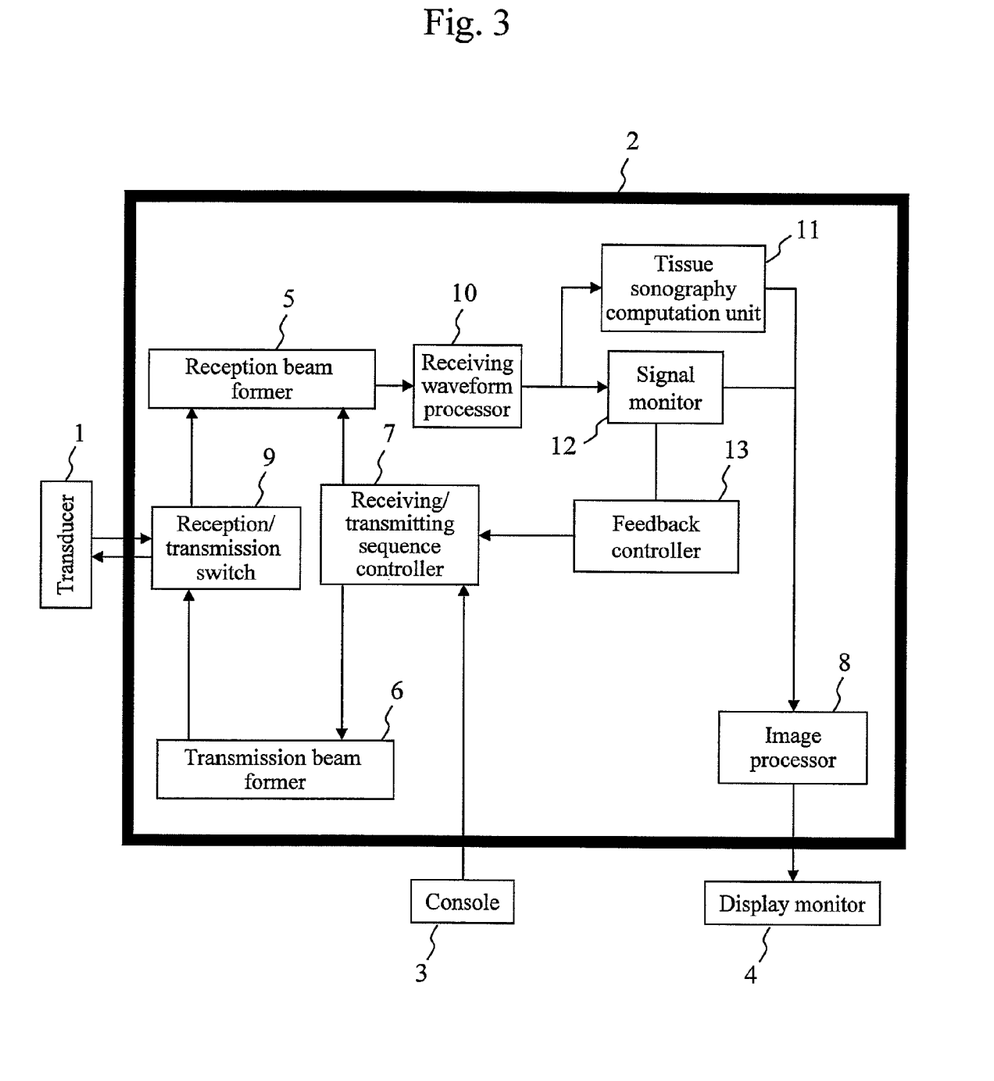
FIG. 3 is a diagram showing an exemplary configuration of an ultrasonic treatment device.

FIG. 3 shows an exemplary configuration of the ultrasonic treatment device to which the above-stated principle is applied. The ultrasonic treatment device has a device configuration in which a transducer 1, a console 3, and a display monitor 4 are connected to a treatment device body 2. The treatment device body 2 has a receiving/transmitting sequence controller 7, a reception beam former 5, a transmission beam former 6, a reception/transmission switch 9, a receiving waveform processor 10, a tissue sonography computation unit 11, a signal monitor 12, a feedback controller 13 and an image processor 8.

The ultrasonic treatment device according to the present invention utilizes a pulse ultrasonic wave to obtain a sonography of a target portion of a diagnosis in the subject to which the phase-change contrast agent has been administered in advance, and displays the obtained tomogram, and blocks the blood flow in the set treatment target area by bubble formation of the phase-change contrast agent.

The transducer 1 is a device that transmits/receives an ultrasonic wave signal to and from the subject. The transducer 1 may be any transducer that can transmit/receive an ultrasonic wave that satisfies conditions required for the bubble formation (formation of bubbles) and bubble growth and can obtain a tomogram of a normal tissue. Further, the transducer need not be a single transducer, and can be constituted by a plurality of transducers combined according to respective purposes.

The console 3 is a console needed for providing various user inputs to provide instruction for the diagnostic machine body 2. For the console 3, a mouse, a stylus pen or other pointing devices, a button, a keyboard or other input devices are employed as appropriate.

The receiving/transmitting sequence controller 7 is a device that determines the transmission condition of the pulse ultrasonic wave. The specifics about the method for determining the transmission condition will be described later. The transmission beam former 6 forms a transmission beam based on a transmission condition provided by the receiving/transmitting sequence controller 7 as well as providing the transmission beam with directionality. The formed transmission beam is provided to the transducer 1, and transmitted to the subject as a transmission echo signal.

The reception beam former 5 is a device that provides reception directionality for the reception echo signal received from the inside of the subject by the transducer 1. The receiving waveform processor 10 is a device that demodulates the reception echo signal obtained at the reception beam former 5. The reception echo signal, after being passed to the tissue sonography computation unit 11, ultimately transmitted to the image processor 8 and supplied as image data to the display monitor 4.

The signal monitor 12 is a device that uses a method described later to extract a bubble component from the reception echo signal and transmits the result of extraction to the feedback controller 13 as the bubble originating signal. The feedback controller 13 is a device that sets the treatment target area based on the bubble originating signal, and prescribes for a region to which the transmission echo signal is to be sent, for the receiving/transmitting sequence controller 7 according to a method described later. The signal monitor 12 also has a function to detect the presence of the blood flow based on the method described later, and sends the result of the detection to the feedback controller 13. The feedback controller 13 also has a function to instruct, based on the position information on the position where the blood flow is detected, the receiving/transmitting sequence controller 7 to successively apply the bubble generation pulse and the bubble stabilization pulse to the concerned position.

Figure 4:
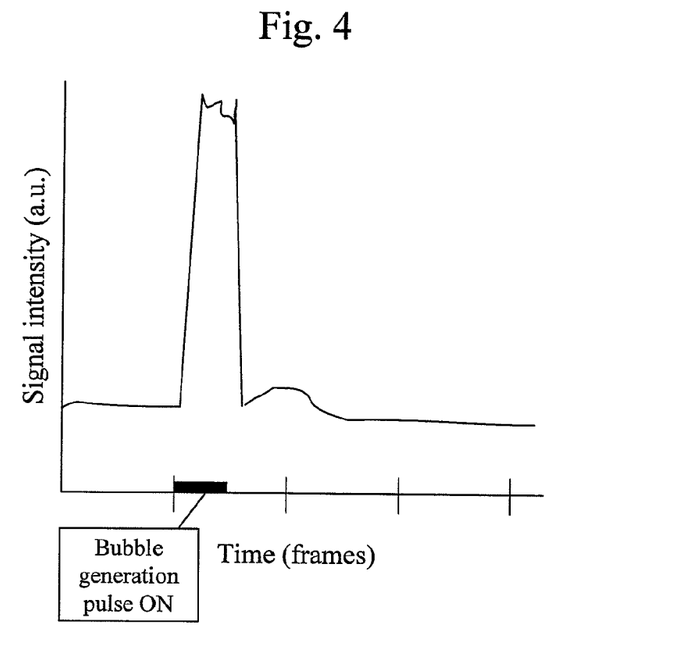
FIG. 4 is a diagram for explaining chronological change in the intensity of an echo signal received from a transient bubble.

Next, one example of a process for extracting the bubble originating signal, which is executed by the signal monitor 12, will be described. The acoustic impedance of a bubble is approximately $0.0004*10^6$ Z (Kg/m$^2$/s), which is clearly different from blood (1.62 z) or a liver (1.64 z). Therefore, when a bubble is formed in the treatment target area, an echo signal of high intensity is detected at the signal monitor 12. As shown in FIG. 4, when, between applications of diagnostic ultrasonic waves for acquiring a tissue sonography, the bubble generation pulse is applied for a time duration for obtaining a tomogram of one section (hereafter referred to as "one frame"), a significant change in the brightness value caused by the bubble formation is detected, as shown in FIG. 4. If, on the detection, signals having brightness higher than a preset threshold value are extracted, only bubble components can be detected.

For employing such processing using a correlation between images, a method for imaging is desirable that can achieve as high frame rate as possible in order to reduce the influence of movement of the body, etc. Examples of such method may include, when a treatment target area is set, dividing imaging regions in the raster direction and reconstructing the image while obtaining differences. Also, a method that employs a combination with a computational function for correcting the body movement is effective. Furthermore, the signal monitor 12 sets a treatment target area based on the bubble originating signal extracted according to the method described above.

Figure 5:
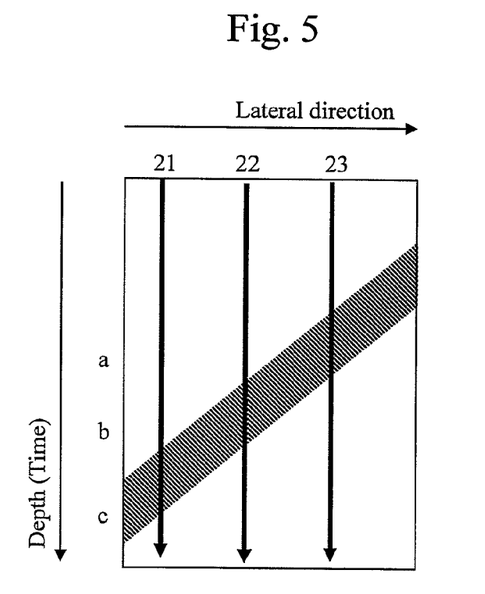
FIG. 5 is a diagram for explaining one exemplary method for extracting position information.

The feedback controller 13, as shown in FIG. 5, extracts position information on the treatment target area based on the depth and lateral direction in which the bubble originating signal is detected, and transmits it to the receiving/transmitting sequence controller 7. A one tissue sonography is composed by transmitting/receiving multiple ultrasonic waves. Depth information of a treatment target area on each ultrasonic wave transmission/reception signal is extracted. In FIG. 5, if the shaded area is the treatment target area, a treatment target area of the ultrasonic wave transmission/reception signal 21 is c, a treatment target area of the ultrasonic wave transmission/reception signal 22 is b, and a treatment target area of the ultrasonic wave transmission/reception signal 23 is a. The receiving/transmitting sequence controller 7 transmits a one pulse, in which the bubble generation pulse and the bubble stabilization pulse converged to respective depths designated on respective transmission/reception signals are successively combined.

Next, one example of a method for blood detection executed by the signal monitor 12 is described. Even if a bubble generation pulse is applied to a treatment target area in the state where the stable bubble has been formed, no significant brightness change is expected to occur at a position where the stable bubble has been formed. On the other hand, a significant brightness rise is expected to occur at a position where a transient bubble is newly to be formed. Therefore, if the change in the brightness value between frames are traced and a rise in the brightness signal by more than a predetermined threshold is extracted, the formation of a new bubble can be detected. This means that a new blood flow can be detected in the treatment target area. In this case, feedback control is performed so that the bubble generation pulse and the bubble stabilization pulse are successively applied to enhance the treatment effect.

Next, an example of another method for blood detection executed by the signal monitor 12 is described. As described above, when the difference between the respective acoustic impedances of biological body and bubble is focused on, it is expected that a significant reduction in the brightness value takes place when an existing bubble fades. Therefore, if the change in the brightness value between frames are traced and a reduction in the brightness signal more than a predetermined threshold is extracted, fading of the bubble can be detected. This means reduction in the effect of treatment. In this case, feedback control is performed so that the bubble generation pulse and the bubble stabilization pulse are successively applied to the concerned region.

The feedback controller 13 has, implemented thereon, a function to transmit position information on a position, on which the above-described bubble formation or fading is detected, to the receiving/transmitting sequence controller 7. The receiving/transmitting sequence controller 7 determines a transmission condition such that the bubble generation pulse and the bubble stabilization pulse converged to a depth designated on the transmission/reception signal is emitted.

Figure 6:
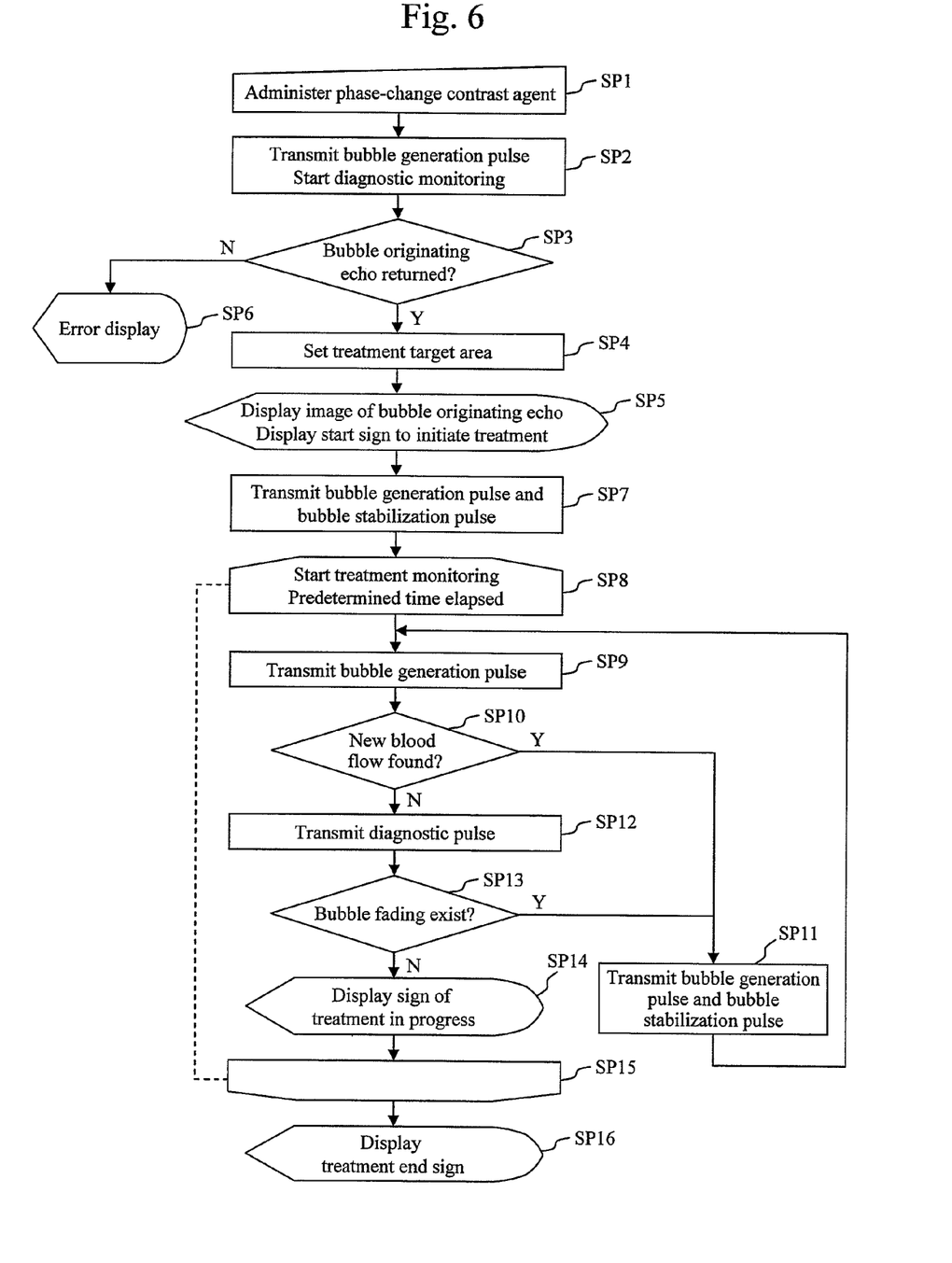
FIG. 6 is a flowchart for explaining one exemplary executing procedure of an embolization treatment using an ultrasonic treatment device.

FIG. 6 shows one example of procedures executed when an embolization treatment is preformed on a tumor portion by the ultrasonic treatment device according to the embodiments of the present invention. After administration of the phase-change contrast agent to a subject (SP1), the transducer 1 is applied to a portion that seems to be a diseased part, such as a tumor, from the surface of the body and the bubble generation pulse is applied (SP2). In the portion where the phase-change contrast agent exists, the phase-change contrast agent undergoes a phase change from liquid to a bubble. The signal monitor 12 determines whether the reception echo signal contains a bubble originating signal (SP3), and sets a portion, where the bubble originating signal is detected, as a "treatment target area" (SP4). Further, the image processor 8 displays an echo image originating from the bubble and received for the set treatment target area on the display monitor 4, and displays a sign for executing the initiation of the embolization treatment on the display monitor 4 (SP5). The treatment setting area can be freely changed by input in the configuration setting for the target area on the display screen. The setting or change of the treatment setting area can be achieved by receiving an operation input to the console 3 at the receiving/transmitting sequence controller 7, and transmit and receive an ultrasonic wave signal to and from the area. When no signal originating from the bubble formation of the phase-change contrast agent is detected, there might be a problem of lack of dose of the phase-change contrast agent, or in the manner in which the transducer 1 is applied. For this case, the ultrasonic wave diagnostic device displays an error message on the display monitor 4 (SP6).

When an embolization treatment for a treatment target area is started, a pulse ultrasonic wave for embolization treatment (that is, a pulse in which the bubble generation pulse and the bubble stabilization pulse are to take place successively) is continuously applied toward the treatment target area (SP7). The transmission of the pulse ultrasonic wave here means that the bubble generation pulse and the bubble stabilization pulse are transmitted in time series as one pulse.

When the embolization treatment is started, treatment monitoring (loop processing) is started (SP8). After the treatment monitoring starts, a pulse ultrasonic wave consisting only of the bubble generation pulse is applied singly (SP9). In parallel therewith, it is determined whether the bubble originating signal is detected in the reception echo signal. If the signal is detected (presence of a new blood flow is detected), the bubble generation pulse and the bubble stabilization pulse are applied only to the region in which the signal is detected (SP10, SP11). The processes according to steps SP9-SP10-SP11 are repeated until no bubble originating signal is detected.

When there appears no new blood flow, the mode shifts to a normal diagnosis mode. When the diagnosis mode is started, a diagnosis pulse is transmitted, and it is monitored whether there is fading of bubbles (SP12, SP13). Upon detection of fading of a bubble (where the effect of the treatment is lowering), the region where the bubble fading is detected is identified, and the bubble generation pulse and the bubble stabilization pulse are applied selectively only to the position (SP11). After the execution of step SP11, the processes of SP9-SP10 are again executed, and the blood flow blocking effect by growth of the bubble is confirmed. These operations of detection, determination and control are performed through the signal monitor 12 and the feedback controller 13.

If the bubble fading is not detected, a sign indicating the treatment being in progress is displayed on the display monitor 4 (SP14). After the execution of the process of SP14, a process to determine whether an arbitrary time set in advance by a user as a time duration for the tumor embolization treatment has ended. When the arbitrary time is not ended, the above-described series of processes are repeated from the process of SP8 (SP15). On the other hand, when the ending of the arbitrary time is detected, the ultrasonic treatment device automatically shifts to a treatment ending operation, and displays a treatment end sign on the display monitor 4 (SP16).

Other Embodiments

The above-described embodiment is described for the case where the bubble generation pulse and the bubble stabilization pulse are generated based on the generation condition shown in table 1. However, the condition for generating the bubble generation pulse and the bubble stabilization pulse are not limited to this, because the optimal generation condition vary according to the depth from the surface of the body in the treatment target area.

Examples of portions where the target diseases may exist include abdominal organ (liver, pancreas, etc), breasts, thyroid, prostate, hysteromyoma, and the like. Of these organs, when an organ located in the deepest part of the body, such as a liver, is the target of the treatment, it is necessary that bubbles are generated and grown at a depth of 10-15 cm from the surface of the body. Where an attenuation rate of the ultrasonic wave within the biological body is 0.6 dB/MHz/cm, and permissible attenuation of the ultrasonic wave is 6 dB, it is desirable to generate the bubble generation pulse and the bubble stabilization pulse with the frequency of 0.6 MHz or less or about 0.5 MHz where the depth is 15 cm. In contrast, for the thyroid or other organs residing in the shallowest portion in the body, the depth is about 1 cm, and therefore it is desirable that the bubble generation pulse and the bubble stabilization pulse are generated at the frequency of 10 MHz.

Additionally, it is desirable that the bubble generation pulse itself is applied at such strength of the ultrasonic wave that does not affect the biological body. As an index value, the Medical Index (MI) value ($=P_{neg}/\sqrt{f}$) is no greater than 1.9 in the focus domain, where $P_{neg}$ is a maximum negative pressure, and f is a central frequency.

It is desirable that the strength of the ultrasonic wave used as the bubble stabilization pulse is equal to or less than the strength of the bubble generation pulse, and the strength is not to generate a bubble when the bubble stabilization pulse are solely applied. On the other hand, it is desirable that the wavelength of the bubble generation pulse is such a short one that will not be affected by the body movement. When the speed of breathing of human is 0.2 Hz, there arises no problem with one cycle duration of 5 ms, which is 1/1000 of the duration of breathing.

The present invention will not be literally limited to the above-described embodiments, and modifications to any elements can be embodied in practice within the extent of the gist of the present invention. For example, the present invention may be used in combination with an ultrasonic wave diagnostic function. Further, many inventions can be made by appropriate combination of the plurality of elements disclosed in the embodiments.

REFERENCE SIGNS LIST

1 . . . transducer
2 . . . treatment device body
3 . . . console
4 . . . display monitor
5 . . . reception beam former
6 . . . transmission beam former
7 . . . receiving/transmitting sequence controller
8 . . . image processor
9 . . . reception/transmission switch
10 . . . receiving waveform processor
11 . . . tissue sonography computation unit
12 . . . signal monitor
13 . . . feedback controller

The invention claimed is:

1. An ultrasonic treatment device that uses a phase-change contrast agent that is in a liquid state at administration and vaporizes once irradiated with an ultrasonic wave, the ultrasonic treatment device comprising:
   a transmission beam former configured to generate an ultrasonic wave transmission beam to generate a bubble generation pulse that causes the phase-change contrast agent to form into a bubble, and a bubble stabilization pulse that increases a diameter of the bubble;
   a transducer configured to transmit the bubble generation pulse and the bubble stabilization pulse to a target area of a subject to which said phase-change contrast agent in said liquid state has been previously administered; and
   a receiving/transmitting sequence controller configured to control switching among the bubble generation pulse, the bubble stabilization pulse, and a diagnostic pulse,
   wherein the receiving/transmitting sequence controller controls switching between transmitting solely the bubble generation pulse and transmit one pulse in which the bubble generation pulse and the bubble stabilization pulse successively take place,
   wherein an intensity of the bubble stabilization pulse is at least an order of magnitude less than an intensity of the bubble generation pulse, and
   wherein said ultrasonic treatment device is configured to irradiate a target area of the subject to which said phase-change contrast agent in said liquid state has been administered with the bubble generation pulse to form a bubble, and after irradiate said target area with said bubble stabilizing pulse with lower intensity than said bubble generation pulse to increase a diameter of the bubble.

2. The ultrasonic treatment device according to claim 1, further comprising:
   a signal monitor configured to detect whether a blood flow is present in the target area; and
   a feedback controller configured to, when blood flow occurrence is detected by the signal monitor, provide a notification to the receiving/transmitting sequence controller such that the bubble generation pulse and the bubble stabilization pulse are to be transmitted only to a portion where the blood flow occurrence is detected by the signal monitor.

3. The ultrasonic treatment device according to claim 1, wherein
   a central frequency of the bubble generation pulse is 0.5-10 MHz, and a pulse duration thereof is within 5 ms.

4. The ultrasonic treatment device according to claim 1, wherein a central frequency of the bubble stabilization pulse is 0.5-10 MHz, and a pulse intensity thereof is weaker than a strength to vaporize the phase-change contrast agent.

5. The ultrasonic treatment device according to claim 1, further comprising a signal monitor configured to detect whether a blood flow is present based on whether an ultrasonic wave signal originating from generation of a new bubble is detected after sole application of the bubble generation pulse to the target area after start of treatment.

6. The ultrasonic treatment device according to claim 1, further comprising a signal monitor configured to extract a bubble component signal from ultrasonic wave detected from the target area detected on application of the diagnostic pulse and detect whether there is fading of the bubble based on a temporal subtraction of a bubble component signal.

7. The ultrasonic treatment device according to claim 6, further comprising a feedback controller configured to, when the fading of the blood flow is detected in the signal monitor, provide a notification to the receiving/transmitting sequence controller such that the bubble generation pulse and the bubble stabilization pulse are transmitted only to a portion where the fading is detected.

8. The ultrasonic treatment device according to claim 1, wherein the bubble stabilization pulse has an ultrasonic wave characteristic selected to vibrate the bubble in a transient bubble state to form a stable bubble.

* * * * *